United States Patent
Townsend

[19]

[11] Patent Number: 5,743,865
[45] Date of Patent: Apr. 28, 1998

[54] KNEE BRACE FOR APPLYING CORRECTIVE LOAD

[75] Inventor: Jeffrey Townsend, Bakersfield, Calif.

[73] Assignee: Townsend Industries, Inc., Bakersfield, Calif.

[21] Appl. No.: 799,488

[22] Filed: Feb. 12, 1997

[51] Int. Cl.$^6$ ........................................ A61F 5/00
[52] U.S. Cl. ........................ 602/26; 602/16; 602/25
[58] Field of Search ........................... 602/5, 16, 20, 602/23, 26, 24, 25

[56] References Cited

U.S. PATENT DOCUMENTS

| | | | |
|---|---|---|---|
| 4,337,764 | 7/1982 | Lerman | 602/26 |
| 4,503,846 | 3/1985 | Martin . | |
| 4,854,308 | 8/1989 | Drillio | 602/26 X |
| 4,966,133 | 10/1990 | Kausek . | |
| 5,018,514 | 5/1991 | Grood et al. | 602/26 X |
| 5,022,391 | 6/1991 | Weidenburner . | |
| 5,131,385 | 7/1992 | Kuehnegger et al. . | |
| 5,135,469 | 8/1992 | Castillo | 602/26 X |
| 5,302,169 | 4/1994 | Taylor . | |
| 5,400,806 | 3/1995 | Taylor . | |
| 5,458,565 | 10/1995 | Tillinghast, III et al. . | |

*Primary Examiner*—Linda C. Dvorak
*Attorney, Agent, or Firm*—Sixbey, Friedman, Leedom & Ferguson; David S. Safran

[57] ABSTRACT

A knee brace is provided which includes a load application device for effectively applying a three point corrective load to the wearer's leg. The load application device includes a load arm pivotally connected to an upper support portion for applying a corrective force to a wearer's thigh and a load arm securing arrangement for adjustably securing the load arm in a desired pivotal position thereby permitting the corrective force to be easily adjusted to adapt to a wide range of leg sizes and shapes. The device also includes a leg support pivotally mounted on the load arm for contacting a wearer's leg and a leg support securing arrangement. Thus, the leg support can be pivotally adjusted to conform to the shape of the wearer's thigh to optimize application of the corrective load while providing a comfortable fit. The load arm and leg support securing arrangements may both be in the form of an arcuate slot and locking pin assembly.

20 Claims, 4 Drawing Sheets

KNEE BRACE FOR APPLYING CORRECTIVE LOAD

BACKGROUND OF THE INVENTION

1. Field of the Invention

This invention relates to orthopedic knee braces, and particularly to an osteoarthritic knee brace capable of effectively applying a corrective load for stabilization of an osteoarthritic knee joint.

2. Description of Related Art

Osteoarthritis is a degenerative disease of the knee joint which results in chronic pain to the subject when the knee joint is loaded. Osteoarthritic pain is caused by an unbalanced loading on the medial or lateral compartment of the knee joint which closes the clearance space forming the compartment between the condyles of the femur and tibia. When there is contact of the condyles in the respective compartment of the knee joint, and particularly dynamic contact, abrasion occurs at the contact surface producing pain in the joint. Relatively mild osteoarthritic pain can be treated with pain reducing drugs. Invasive surgery, however, has often been the treatment of choice for more advanced cases of osteoarthritis causing debilitating pain. Surgery, nevertheless, may not provide effective long-term correction of the condition because degeneration of the knee joint frequently continues even after initial surgical correction. Accordingly, follow-up surgical procedures can be required to restore and maintain the joint, thereby diminishing the desirability of surgery as a treatment alternative.

Thus, a need exists for an effective, noninvasive means of relieving pain associated with the degenerative diseases of the knee joint. U.S. Pat. No. 5,458,565 to Tillinghast, III discloses an osteoarthritic knee brace including an upper and lower arm members rotatably connected to each other by a rotary hinge assembly. An inflatable pad is mounted adjacent the hinge assembly for abutment against the knee joint. The upper and lower arm members form a leaf spring for applying a treatment force to the lateral side of the knee joint via the flexible pad. The treatment force is opposed by two resultant forces acting on the medial side of the leg. The treatment force can be adjusted by varying the amount of inflation of the pad.

However, osteoarthritis of the leg also can result in bone deformation, so that the femur extends from the knee joint at extreme angles from the axis of the leg. Also, it is common for persons suffering from osteoarthritis to possess legs which are soft due to their inability to exercise leading to attrification of leg muscles and/or accummulations of fatty tissue. The upper and lower members of the knee brace of the '565 patent are not laterally adjustable. Therefore, the '565 knee brace cannot be readily mounted on such deformed and/or large legs without redesigning the brace for a specific leg. Moreover, use of the bent leaf spring requires the brace be designed for a specific size or limited range of sizes of legs to achieve the desired range of treatment force via adjustment of the pads. In essence, the shape and size of the '565 leaf spring and upper and lower members during manufacture of the brace, and the size of the leg, determine the range of treatment force available for a specific size brace. Application of the brace to overly large or deformed legs could result in an unacceptably high magnitude of available treatment force. In addition, the degree of inflation of the pad and the compressibility of the air with which it is inflated leads to only a very limited range of adjustment in the magnitude of the treatment force being obtainable.

U.S. Pat. Nos. 5,400,806 and 5,302,169 to Taylor discloses a post operative knee brace including a pair of arms connected by and extending in opposite directions from, a pivotable joint for permitting a knee to pivot. Each arm includes a joint allowing controlled inclination of each arm toward the leg. However, this brace is to be used in place of a cast to securely support and brace a leg which has been repaired by surgery and, therefore, is not used to apply a corrective load to a leg to reposition the leg bones. Moreover, the Taylor brace results in the application of only two force points, above and below the knee joint. Thus, the Taylor device is incapable of imparting a sufficient force to the leg necessary to correct an existing misalignment condition. In addition, this brace must be specially designed for each application and is not readily adaptable to legs of various sizes.

U.S. Pat. No. 5,131,385 to Kuehnegger et al. is noted for disclosing an orthesis for the knee which includes two joints which are disposed at the sides of the knee, and arms which extend across the knee above and below the knee cap to connect the joints. A centrally disposed, longitudinally extending rail extends from each of the arms to support a respective leg strap. Each rail is secured to the respective arm by means of two screws extending through two holes in the tongue which are larger than the screws. Thus, the rail can be swung laterally across the leg to reposition the strap to accommodate the shape of the leg. However, the rail and strap assembly is not used to apply a corrective load. Also, the oversized hole design does not permit sufficient lateral movement of the strap to accommodate many deformed and/or soft legs.

Other conventional designs for knee braces are disclosed in U.S. Pat. Nos. 4,503,846; 4,966,133; and 5,022,391.

The above-discussed problems with the prior art indicate that the need exists for an osteoarthritic knee brace effectively applying a corrective force to a deformed or soft leg while permitting simple adjustment of the corrective force.

SUMMARY OF THE INVENTION

It is an object of the present invention to overcome the disadvantages of the prior art and to provide a knee brace capable of effectively applying a corrective load to a leg.

It is another object of the present invention to provide a knee brace for treating osteoarthritis which adjusts to a wide range of leg sizes and shapes.

It is yet a further object of the present invention to provide a osteoarthritic knee brace capable of being simply and easily adapted to apply a corrective load to a deformed or soft large leg.

Another object of the present invention is to provide an osteoarthritic knee brace having a leg support with a substantial leg contact area and extending sufficiently along the side of the leg to maximize the comfort to the wearer's leg while effectively applying a corrective force.

It is still another object of the present invention to provide an osteoarthritic knee brace capable of applying a three point force to the leg to achieve an optimum corrective load on the knee joint.

Yet another object of the present invention is to provide an osteoarthritic knee brace capable of applying a corrective load to a leg which permits the corrective load to be easily adjusted.

Still another object of the present invention is to provide an osteoarthritic knee brace capable of applying either a varus or a valgus force upon the knee.

3

These and other objects that will become apparent in the following description are achieved in accordance with preferred embodiments of the invention. In particular, a knee brace is provided with an upper support portion including an upper frontal cross member connecting a lateral femoral strut with a medial femoral strut, a lower support portion including a lower frontal cross member connecting a lateral strut with a medial tibial strut, a joint mechanism connecting the upper support portion and the lower support portion for permitting bending movement of a wearer's leg, and a load application device connected to the upper portion for applying a corrective load to the wearer's leg.

The load application device includes a load arm pivotally connected to the upper support portion, a load arm securing arrangement for adjustably securing the load arm against pivotal movement relative to the upper support portion, and a "paddle" or leg support mounted on the load arm for contacting a wearer's leg and applying the corrective load to the side of the wearer's leg. The corrective load is maintained by securing the load arm against pivotal movement. The corrective load may include a corrective force imparted on one side of the wearer's leg by the upper support portion, a complementary force imparted to the same side of the wearer's leg by the lower support portion and a force imparted to an opposite side of a wearer's knee joint by the condyle pad on the joint mechanism.

The load arm securing arrangement may include an arcuate slot formed in either the load arm or the upper frontal cross member, and a pin mounted on the other of the load arm and the upper frontal cross member and extending into the slot for movement along the slot. The load arm securing arrangement may further include a locking nut for engaging the pin to prevent pivotal movement of the load arm. The leg support may be pivotally mounted on the load arm and a leg support securing arrangement may be provided. The leg support securing arrangement may include an arcuate slot formed in either the load arm or the leg support, and a pin mounted on the other of the load arm and leg support for extending into the slot for movement along the slot. The leg support securing arrangement may include a locking nut for engaging the pin to prevent pivotal movement of the leg support. Also, the load arm is capable of pivoting through an angular range of at least 40°, preferably at least 54°. The leg support is also capable of pivoting through an angular range of at least 40°, preferably at least 54°.

In addition, the leg support includes a front portion positioned on a front of the wearer's leg and a side portion extending along a side of a wearer's leg wherein the side portion is capable of being pivotally positioned to conform to the wearer's leg at all pivotal positions of the load arm. The side portion is formed of a rigid material extending from the mounting portion along a rear quarter portion of the wearer's leg to form an enlarged support surface. The mounting portion has an axial width defined by upper and lower transverse edges while the rigid side portion includes an axial width defined by respective upper and lower transverse edges. The axial width of the side portion is larger than the axial width of the mounting portion in that both the upper and lower edges of the side portion are positioned axially outwardly from the upper and lower edges of the mounting portion.

These and further objects, features and advantages of the present invention will become apparent from the following description when taken in connection with the accompanying drawings which, for purposes of illustration only, show several embodiments in accordance with the present invention.

4

DETAILED DESCRIPTION OF THE PREFERRED EMBODIMENTS

Figure 1:
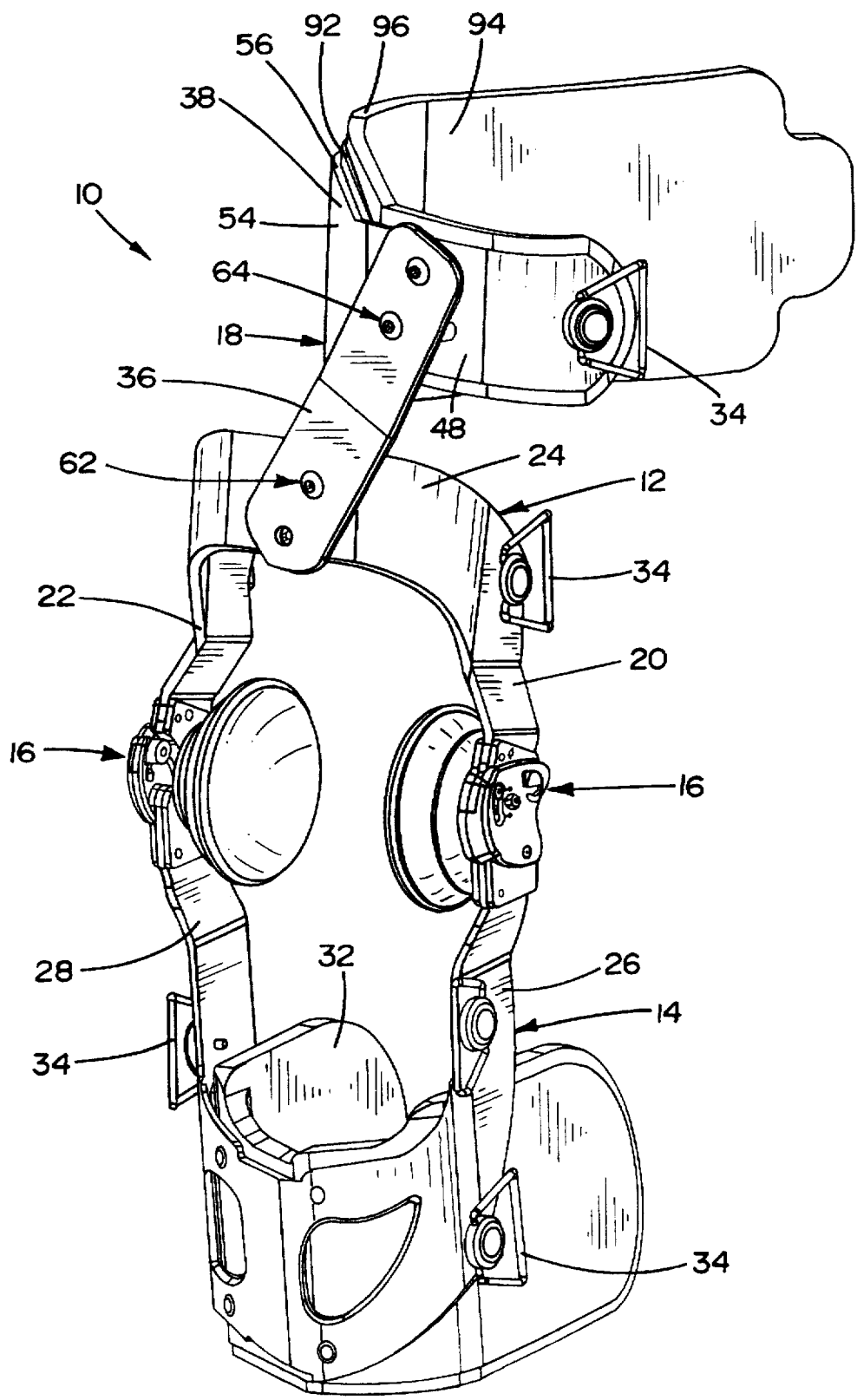
FIG. 1 is a perspective view of a knee brace in accordance with the present invention.
Figure 2:
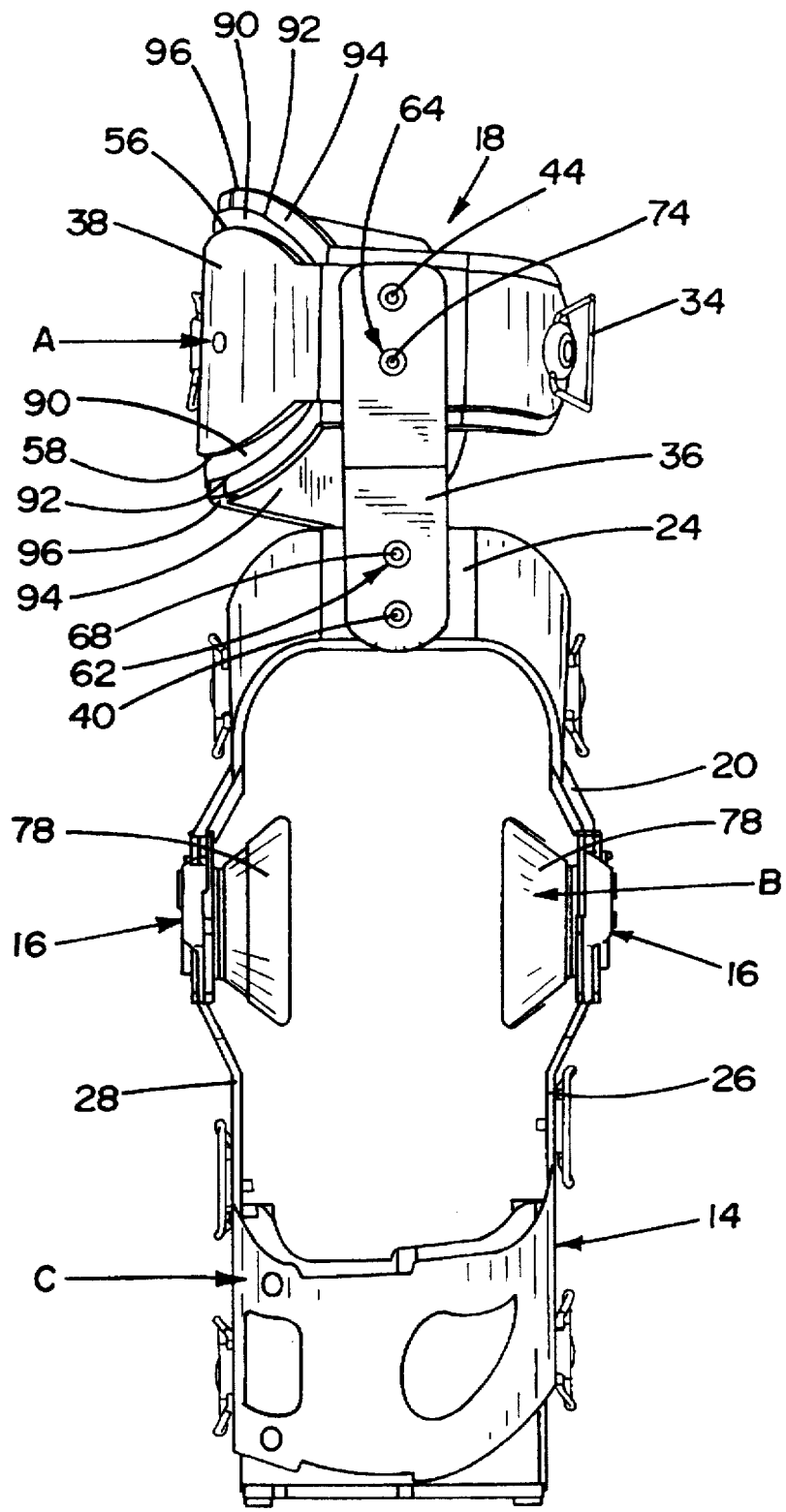
FIG. 2 is a front view of the knee brace of FIG. 1.

Referring to FIGS. 1 and 2, there is shown a knee brace, indicated generally at 10, designed in accordance with the present invention. Knee brace 10 includes an upper support portion 12 for positioning adjacent a wearer's proximal thigh, a lower support portion 14 for positioning adjacent the wearer's calf and a joint mechanism 16 for pivotally connecting upper support portion 12 and lower support portion 14. Knee brace 10 also includes a load application device 18 for effectively applying a corrective load to the wearer's leg for treating, for example, osteoarthritis in the wearer's knee joint.

Upper support portion 12 includes a lateral femoral strut 20, a medial femoral strut 22 and an upper frontal cross member 24 connecting the upper ends of each strut 20, 22 and extending across the front of the brace. Similarly, lower support portion 14 includes a lateral tibial strut 26, a medial tibial strut 28 and a lower frontal cross member 30 connecting the lower ends of struts 26, 28 and extending across the front of the knee brace. Upper and lower support portions 12, 14 are sized to receive a wearer's leg and are generally made of a rigid material, such as aluminum, titanium, or fiber and resin composites. Lower support portion 14 desireably includes a resilient pad or cushion 32 for creating a comfortable fit against a wearer's leg. Knee brace 10 also includes buckles 34 attached to upper support portion 12, lower support portion 14 and load application device 18 for connection to attachment straps (not shown) for securing a knee brace to a wearer's leg.

Joint mechanism 10 may be any conventional joint mechanism that permits swinging movement of the femoral struts 20, 22 relative to the tibial struts 26, 28. However, joint mechanism 10 is preferably one of the present inventor's patented joint mechanisms, such as the improved joint mechanism disclosed in U.S. Pat. No. 5,259,832, the contents of which are incorporated herein by reference to the extent necessary to complete an understanding of this invention. This preferred joint mechanism permits the natural glide and roll motion present in the normal knee. This duplication of physiological knee motion allows the tibial and femoral members to remain in contact with the respective leg limb throughout the entire range of motion thereby providing patient comfort while allowing the corrective load, discussed more fully hereinbelow, to be applied in the proper areas. Also, this duplication of anatomical motion achieved by the preferred joint mechanism serves to minimize pistoning of the brace on the leg thereby providing secure suspension.

Figure 3:
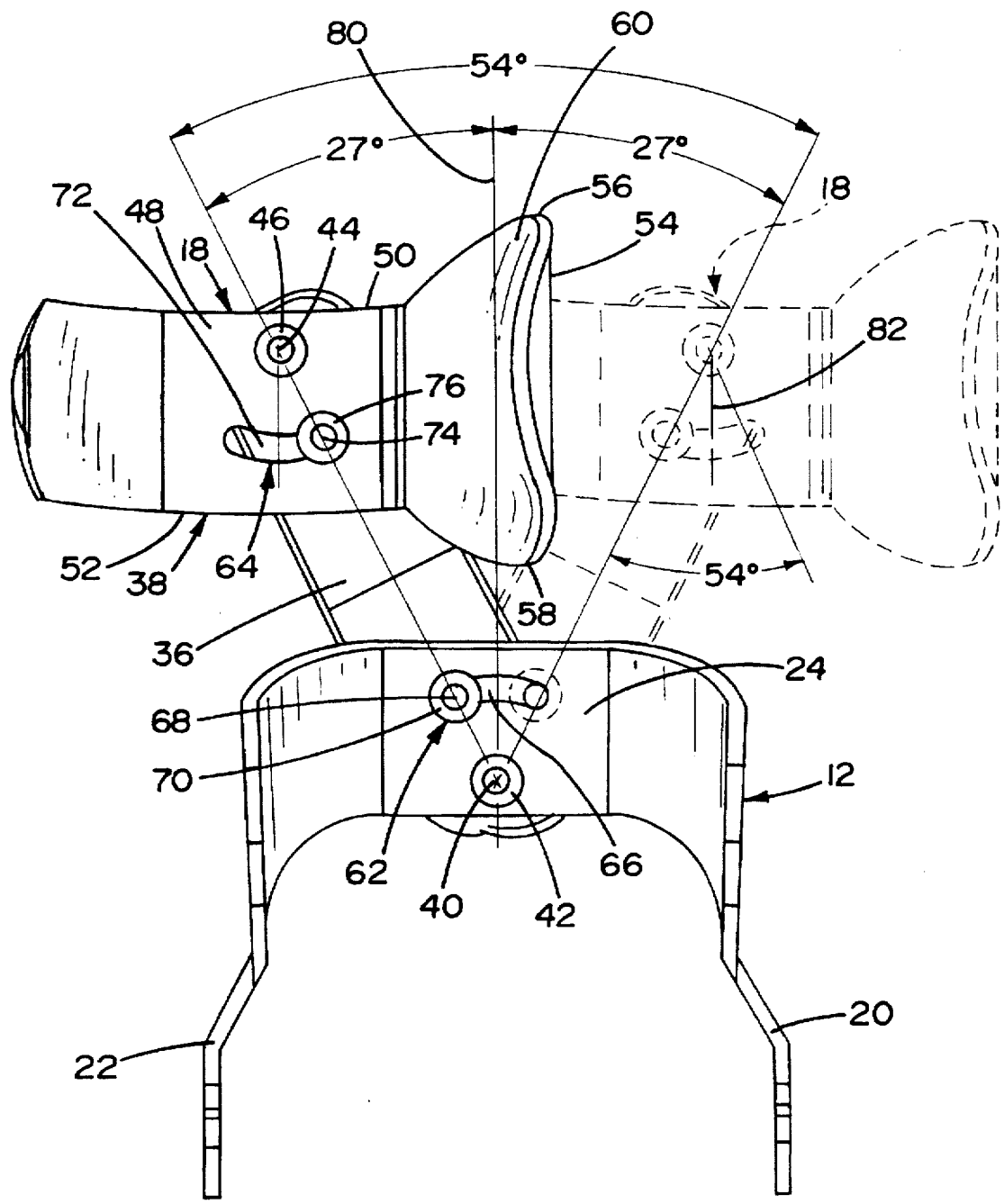
FIG. 3 is a rear view of the upper support, load arm and leg support of the knee brace of FIG. 1 showing the load arm positioned in two positions.

Load application device 18 includes a load arm 36 pivotally connected at one end to upper frontal cross member 24 and a "paddle," i.e., leg support 38, pivotally connected to a second end of load arm 36. Load arm 36 is a generally flat, rectangular shaped arm formed of a rigid material capable of effectively transmitting loads between leg support 38 and upper support portion 12. Load arm 36 is pivotally connected to the central area of upper frontal cross member 24 by any conventional securing means which permits pivotal movement between load arm 36 and upper frontal cross member 24. For example, an Allen head bolt can serve as a pivot pin 40 to which a nut 42 is threaded, pivot pin 40 being mounted to load arm 36 extending through a hole formed in it and in upper frontal cross member 24 to engage pivot nut 42 on the rear side of cross member 24, as shown in FIG. 3. Leg support 38 is attached to an opposite end of load arm 36 in a similar manner by, e.g., an Allen head bolt serving as pivot pin 44 which extends through apertures in load arm 36 and leg support 38 to engage a pivot nut 46.

Referring to FIG. 3, leg support 38 includes a mounting portion 48 defined by upper and lower transverse edges 50, 52, respectively, and a side portion 54 integrally formed on mounting portion 48. Side portion 54 is defined by upper and lower transverse edges 56, 58 respectively, which are positioned axially outwardly above and below transverse edges 50, 52 of mounting portion 48 so as to form an enlarged support surface 60. Enlarged support surface 60 is designed with a sufficient surface area necessary to effectively diffuse or distribute the pressure between side portion 54 and the wearer's leg over a large area of the wearer's leg so as to avoid localized pressure points thereby maximizing the comfort to the wearer's leg. Also, side portion 54 extends a sufficient distance around the wearer's leg so as to overlap the rear quarter of a wearer's leg thereby ensuring effective application of a corrective force to the femur.

Knee brace 10 is designed with load application device 18 for applying a three point corrective load to the wearer's leg, i.e. a three point pressure system, to optimize the desired corrective effect on the knee joint. As shown in FIG. 2, the corrective load includes a corrective force A applied to one side of a wearer's thigh by leg support 38. The application of corrective force A results in a force B applied to the knee joint on the opposite side of the leg from the corrective force by joint supports indicated at 78. Corrective force A also results in application of a complementary force C to the calf area of the leg by the lower support portion 14 on the same side of the leg as corrective force A. This three point pressure system can be used to effectively treat osteoarthritis in the knee joint by applying either a varus or valgus force to the knee joint.

The pivoting action of load arm 36 relative to cross member 24 permits leg support 38 to be moved into a wide range of lateral positions, as shown in FIG. 3, to accommodate legs of different shapes and sizes. Also, the pivoting action of leg support 38 relative to load arm 36 permits side portion 54 of leg support 38 to be moved into various angular positions to accommodate the contour of the wearer's thigh thus improving application of the corrective force while maximizing comfort to the wearer. Specifically, as shown in FIG. 3, load arm 36 can be pivoted approximately 27° in both directions from the central longitudinal axis 80 of knee brace 10 resulting in a total range of adjustment of 54°. Likewise, leg support 38 may be pivoted approximately 27° in both directions from a vertical longitudinal axis 82 extending through pivot pin 44 as shown in FIG. 3, to create a total pivoting range of 54°. While a 54° range of pivotal adjustment is preferred, providing a range of at least 40° for both load arm 36 and leg support 38 also achieves significant benefits. Specifically, the range of adjustment achieved by the pivoting of the load arm 36 and leg support 38 enables the present knee brace to easily and effectively apply, set and adjust corrective loads to legs having a variety of shapes and sizes while providing a comfortable fit.

Load application device 18 further includes a load arm securing arrangement 62 for securing load arm 36 in a desired pivotal position, and a leg support securing arrangement 64 for securing leg support 38 in a desired pivotal position relative to the wearer's leg and load arm 36. As shown in FIG. 3, load arm securing arrangement 62 includes an arcuate slot 66 formed in upper frontal cross member 24 immediately above the pivot point for load arm 36. Load arm securing arrangement 62 also includes, e.g., an Allen head bolt serving as a locking pin 68 extending through load arm 36 and slot 66 and a locking nut 70 for engaging locking pin 66 and upper support portion 12 so as to securably hold locking pin 68 in a predetermined position along slot 66, thereby fixing load arm 36 in a predetermined pivotal position. Likewise, leg support securing arrangement 64 includes an arcuate slot formed in mounting portion 48 of leg support 38, an Allen head bolt serving as a locking pin 74 extending through load arm 36 and arcuate slot 72, and a locking nut 76 threaded onto locking pin 74 to fix leg support 38 in a desired pivotal position. Locking pins 68, 74 and locking nuts 70, 76 may be any conventional fastening device capable of securing load arm 36 and leg support 38 against pivotal movement during the application of corrective loads.

Pivot pin 44, pivot nut 46 and leg support securing arrangement 64 are preferably designed to permit leg support to be reversibly mounted on load arm 36 to allow the same leg support to be used to apply either a medial or lateral force to the same leg as desired. Specifically, pivot pin and nut 44, 46 are removably secured and pivot pin 74 sized to be insertable into arcuate slot 72. As such, pivot nut 46 and leg support securing arrangement 64 can be removed allowing the leg support 38 to be detached from load arm 36 and rotated 180 degrees from the orientation shown in FIG. 3. Leg support 38 is then reattached to load arm 36 so that pivot pin 44 extends through arcuate slot 72 and locking pin 74 extends through the aperture previously occupied by pivot pin 44 and the locking nut 76 and pivot nut 46 then reattached to the corresponding pins. In this case, the leg support securing arrangement 64 becomes the pivot pin and the pivot pin and nut become leg support securing arrangement.

Figure 4A:
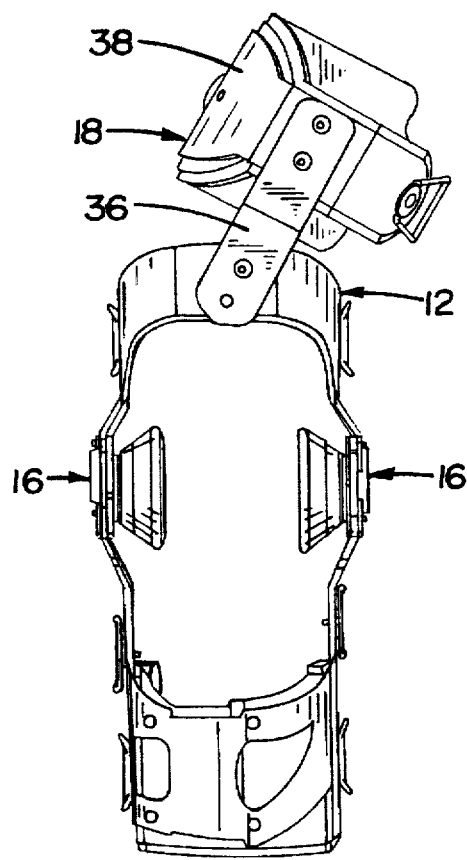
FIGS. 4a–4b are front views of the knee brace of FIG. 1 showing the leg support positioned in two different positions.
Figure 4B:
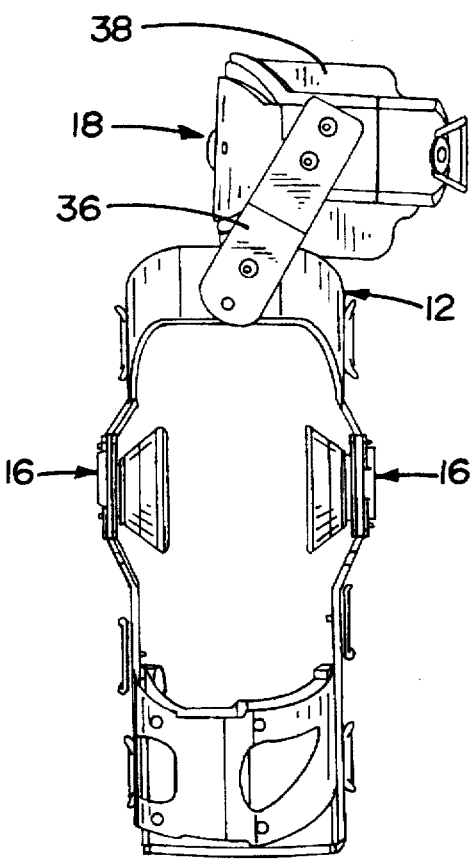
Figure 5A:
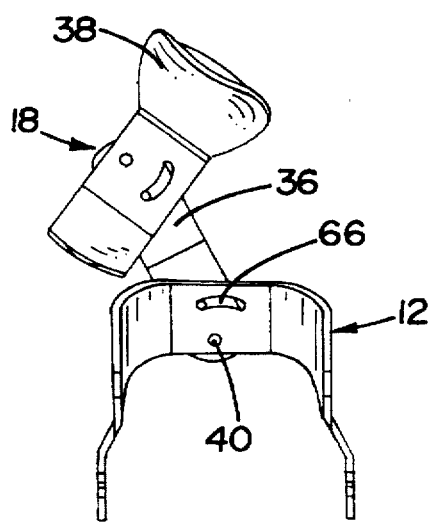
FIGS. 5a–5b are rear views of the upper support, load arm and leg support of the present knee brace showing the load arm and leg support positioned in different positions.
Figure 5B:
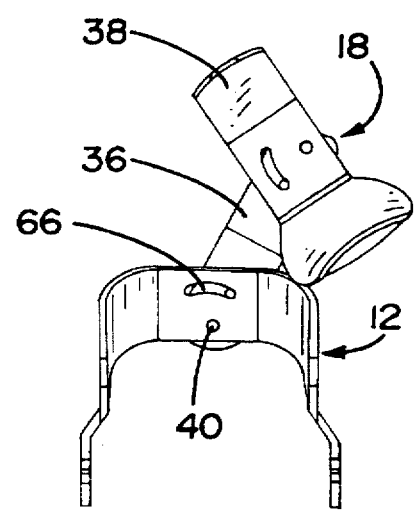

By incorporating load application device 18, the present invention further optimizes the application and effect of the corrective loading. Specifically, as shown in FIGS. 3 and 4a–4b, the load arm 36 and leg support 38 can be moved or adjusted into an infinite number of positions. As a result, knee brace 10 can be applied to legs of various sizes and shapes, and adequate loading applied despite any softness of the leg due to loss of muscularity, accummulation of fatty tissue and/or weakness of the bones due, e.g., due to osteoporosis. In addition, the load application device 18 permits the corrective load on the leg to be easily adjusted to achieve the precise desired loading. In addition, by making leg support 38 reversible, the present knee brace 10 can be used on either leg to apply a lateral force to the medial thigh or medial force to the lateral thigh area of the leg without major disassembly, replacement of components or exchanging of braces.

By forming leg support 38 with an enlarged support surface 60, the present knee brace effectively diffuses the force over a large area of the wearer's leg thereby avoiding pressure points and creating a more comfortable knee brace.

Also, to further increase comfort, as most easily seen in FIGS. 1 and 2, an inner surface of the rigid side portion 54 is covered by a semi-rigid liner member 90 having an axial width that is greater than the axial width of said rigid side portion 54 so that upper and lower edges 92 of liner member 90 extend beyond the upper and lower transverse edges 56, 58 of the rigid side portion 54. Furthermore, an inner side of the semi-rigid liner member 90 is covered by a soft inner cushion member 94 having an axial width that is greater than the axial width of said semi-rigid finer member so that upper and lower edges 96 of soft inner cushion member 94 extend beyond the upper and lower transverse edges 92 of the semi-rigid liner member 90. As a result, the required rigidity can be achieved without having any edges which can uncomfortably dig into the skin of the wearer's leg.

In use, knee brace 10 is mounted on the front of a wearer's leg with joint mechanism 16 positioned on each side of the knee joint. During this time, all of the nuts are loosely mounted on their respective pins. Attachment straps (not shown), which are attached to buckles 34, are then secured around the wearer's distal calf and proximal thigh leg portions and tightened to secure knee brace 10 in position on the wearer's leg. Load arm 36 is then pivoted around pivot pin 40 to laterally position the leg support 38 in abutment with the wearer's thigh. The corrective load on the wearer's leg is then applied by applying an inward force against side portion 54 so as to press side portion 54 against the wearer's thigh with a force corresponding to the desired corrective loading. While maintaining the force on side portion 54, pins 40, 68 and nuts 42, 70 are tightened to secure load arm 36 against pivotal movement relative to cross member 24, thus fixing the leg support 38 relative to the wearer's thigh while achieving a desired corrective loading. During this process, the leg support 38 will have pivoted around pivot pin 44 in conformance with the leg surface against which it is pressed, the enlarged support surface 60 being positioned in flush abutment with the wearer's thigh. The pins 44, 74 and nuts 46, 76 are then tightened to secure leg support 38 in the desired pivotal position relative to load arm 36 and the wearer's thigh.

While various embodiments in accordance with the present invention have been shown and described, it is understood that the invention is not limited thereto, and is susceptible to numerous changes and modifications as known to those skilled in the art. Therefore, this invention is not limited to the details shown and described herein, and includes all such changes and modifications as are encompassed by the scope of the appended claims.

We claim:

1. A knee brace comprising:
    an upper support portion including an upper frontal cross member connecting a lateral femoral strut with a medial femoral strut;
    a lower support portion including a lower frontal cross member connecting a lateral tibial strut with a medial tibial strut;
    a joint mechanism connecting said upper support portion and said lower support portion for permitting bending movement of a wearer's leg;
    load application means connected to said upper support portion for applying a corrective load to a side of the wearer's leg, said load application means including a load arm pivotally connected to said upper support portion, a load arm securing means for adjustably securing said load arm against pivotal movement relative to said upper support portion, a leg support pivotally mounted on said load arm for contacting a wearer's leg, and a leg support securing means for adjustably securing said leg support against pivotal movement relative to said load arm, said load arm being securable against pivotal movement relative to said upper support portion by said load arm securing means and being securable against pivotal movement relative to said leg support by said leg support securing means in each position within a range of relative angular positions for maintaining an applied corrective load and for producing a proper fit of the knee brace on the wearer's leg.

2. The knee brace of claim 1, wherein said load arm securing means includes an arcuate slot formed in one of said load arm and said upper frontal cross member, and a pin mounted on the other of said load arm and said upper frontal cross member and extending into said slot for movement along said slot.

3. The knee brace of claim 2, wherein said load arm securing means further includes a locking nut for engaging said pin to prevent pivotal movement of said load arm.

4. The knee brace of claim 2, wherein said leg support securing means includes an arcuate slot formed in one of said load arm and said leg support, and a pin mounted on the other of said load arm and said leg support and extending into said slot for movement along said slot.

5. The knee brace of claim 4, wherein said leg support securing means further includes a locking nut for engaging said pin to prevent pivotal movement of said leg support.

6. The knee brace of claim 1, wherein said range of relative angular positions for said load arm relative to said upper support portion is an angular range of at least 40°.

7. The knee brace of claim 6, wherein said range of relative angular positions for said load arm relative to said leg support is an angular range of at least 54°.

8. The knee brace of claim 1, wherein said leg support includes a mounting portion positioned on a front of the wearer's leg and a side portion extending along a side of a wearer's leg, said side portion capable of being pivotally positioned to conform to the wearer's leg at all pivotal positions of said load arm.

9. The knee brace of claim 8, wherein said side portion is formed of a rigid material extending from said mounting portion along a rear quarter portion of the wearer's leg to form an enlarged support surface.

10. The knee brace of claim 9, wherein said mounting portion has an axial width defined by upper and lower transverse edges, said rigid side portion having an axial width, defined by upper and lower transverse edges, which is larger than said axial width of said mounting portion, wherein said upper and said lower edges of said side portion are both positioned axially outwardly from said upper and lower edges of said mounting portion; wherein an inner side of at least said rigid side portion is covered by a semi-rigid liner member having an axial width that is greater than the axial width of said rigid side portion; and wherein an inner side of said semi-rigid liner member is covered by a soft inner cushion member having an axial width that is greater than the axial width of said semi-rigid finer member.

11. A knee brace for treating osteoarthritis comprising:
    an upper support portion including an upper frontal cross member connecting a lateral femoral strut with a medial femoral strut;
    a lower support portion including a lower frontal cross member connecting a lateral tibial strut with a medial tibial strut;
    a joint mechanism connecting said upper support portion and said lower support portion for permitting bending movement of a wearer's leg;

load application means connected to said upper support portion for applying a corrective load to one side of the wearer's leg by said upper support portion, means for applying a complementary force to said one side of said wearer's leg at said lower support portion and means for imparting a force to a wearer's knee joint by said joint mechanism at an opposite side of the leg from the side to which said corrective load and complementary force is applied;

wherein said load application means comprises a load arm pivotally connected to said upper frontal cross member, a load arm securing means for adjustably securing said load arm against pivotal movement relative to said upper support portion, a leg support mounted on said load arm for contacting a wearer's leg and applying the corrective load to the side of the wearer's leg, said load arm being securable against pivotal movement relative to said leg support by said leg support securing means in each position within a range of relative angular positions for maintaining an applied corrective load.

12. The knee brace of claim 11, wherein said load arm securing means includes an arcuate slot formed in one of said load arm and said upper frontal cross member, and a pin mounted on the other of said load arm and said upper frontal cross member and extending into said slot for movement along said slot.

13. The knee brace of claim 12, wherein said load arm securing means further includes a locking nut for engaging said pin to prevent pivotal movement of said load arm.

14. The knee brace of claim 12, wherein said leg support is pivotally mounted on said load arm and said load application means further includes a leg support securing means including an arcuate slot formed in one of said load arm and said leg support, and a pin mounted on the other of said load arm and said leg support and extending into said slot for movement along said slot.

15. The knee brace of claim 14, wherein said leg support securing means further includes a locking nut for engaging said pin to prevent pivotal movement of said leg support.

16. The knee brace of claim 11, wherein said load arm is capable of pivoting through an angular range of at least 40°.

17. The knee brace of claim 16, wherein said leg support is capable of pivoting through an angular range of at least 54°.

18. The knee brace of claim 11, wherein said leg support includes a mounting portion positioned on a front of the wearer's leg and a side portion extending along a side of a wearer's leg, said side portion capable of being pivotally positionable to conform to the wearer's leg at all pivotal positions of said load arm.

19. The knee brace of claim 18, wherein said side portion extends from said mounting portion along a rear quarter portion of the wearer's leg to form an enlarged contact surface.

20. The knee brace of claim 19, wherein said mounting portion has an axial width defined by upper and lower transverse edges, said rigid side portion having an axial width, defined by upper and lower transverse edges, which is larger than said axial width of said mounting portion, wherein said upper and said lower edges of said side portion are both positioned axially outwardly from said upper and lower edges of said mounting portion; wherein an inner side of at least said rigid side portion is covered by a semi-rigid liner member having an axial width that is greater than the axial width of said rigid side portion; and wherein an inner side of said semi-rigid liner member is covered by a soft inner cushion member having an axial width that is greater than the axial width of said semi-rigid liner member.

* * * * *